(12) United States Patent
Gross

(10) Patent No.: US 7,438,202 B2
(45) Date of Patent: Oct. 21, 2008

(54) HAIR REMOVING APPARATUS

(75) Inventor: Jeroen Alexander Gross, The Hague (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 510 days.

(21) Appl. No.: 10/536,920

(22) PCT Filed: Nov. 6, 2003

(86) PCT No.: PCT/IB03/05066

§ 371 (c)(1),
(2), (4) Date: May 31, 2005

(87) PCT Pub. No.: WO2004/050313

PCT Pub. Date: Jun. 17, 2004

(65) Prior Publication Data

US 2006/0208001 A1    Sep. 21, 2006

(30) Foreign Application Priority Data

Dec. 3, 2002  (EP) .................................. 02080062

(51) Int. Cl.
*B65D 37/00* (2006.01)
*B26B 19/40* (2006.01)

(52) U.S. Cl. .......................................... 222/214; 30/41

(58) Field of Classification Search .................... 30/41, 30/41.5; 222/190, 191, 630, 632, 206, 209, 222/212, 213, 400.5, 214; 134/115 R; 132/112, 132/119.1, 272

See application file for complete search history.

(56) References Cited

U.S. PATENT DOCUMENTS

| 3,103,299 | A | * | 9/1963 | Werft | 222/1 |
| 3,299,506 | A | * | 1/1967 | Gwinn | 30/41 |
| 4,023,269 | A | * | 5/1977 | Lopez, Jr. | 30/41 |
| 4,031,618 | A | | 6/1977 | Mansfield | |
| 5,121,541 | A | * | 6/1992 | Patrakis | 30/41 |
| 6,131,288 | A | * | 10/2000 | Westerhof et al. | 30/41 |
| 6,594,905 | B2 | * | 7/2003 | Furst et al. | 30/41 |

FOREIGN PATENT DOCUMENTS

| DE | 1703761 | 3/1972 |
| DE | 199 07 224 A1 | 8/2000 |
| DE | 19907224 A1 | 8/2000 |

* cited by examiner

*Primary Examiner*—Kenneth E. Peterson
*Assistant Examiner*—Phong Nguyen

(57) ABSTRACT

A hair removing apparatus has hair removing device (13) for at least partially removing hair projecting from a skin; a liquid channel (16) leading to a liquid outlet (12); a pump (5) for causing liquid displacement through the liquid channel to the liquid outlet; a motor (1) coupled to the hair removing device (13); a transmission coupled to the motor (1) and to the pump (5); and a control structure (4,7-9) operable between at least a first and a second operating condition for dispensing liquid at different rates. The control structure (4,7-9) is arranged for controlling amounts of movement transmitted by the transmission to the pump such that, in the first and second operating conditions, different amounts of movement are transmitted by the transmission to the pump.

10 Claims, 3 Drawing Sheets

HAIR REMOVING APPARATUS

Figure 1:
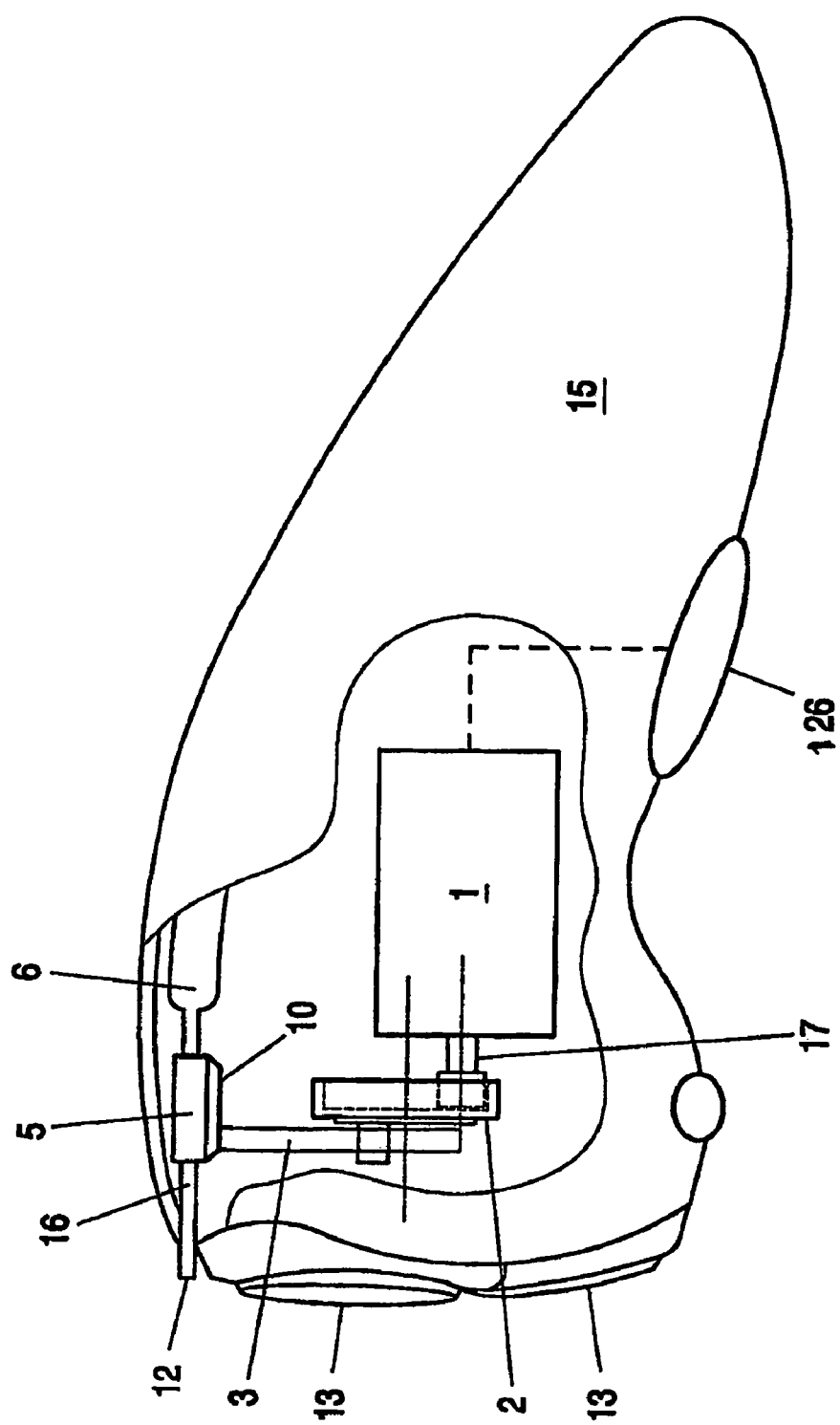

The invention relates to an electric personal care device such as for example a shaver, an epilator, or an oral care device.

From German patent application 199 07 224, a liquid container for a hair removing apparatus is known, which liquid container is provided with a pump. The pump is driven by the electromotor of the hair removing apparatus via a pivotable double rocker arm of the hair removing apparatus, of which one arm repetitively pushes in a resilient membrane of the pump. The pump is attached to the liquid container and can be activated and deactivated by shifting the container with respect to the housing of the hair removing apparatus to which the double rocker arm and the electromotor are attached. By shifting the container in one direction, the membrane is caused to be engaged by the reciprocatively moving arm of the double rocker arm causing the pumping action of the membrane to be driven. If the container is shifted back, the membrane is disengaged again from the double rocker arm so that the pumping action is discontinued. The liquid is dispensed from a porous dispensing member upon contact between that dispensing member and the skin. Liquid flow through a return channel back to the container causes the liquid pressure in the dispensing member to be limited such that the liquid is not dispensed from the dispensing member in absence of contact to the skin. The dosage of liquid can be controlled by varying the exposed surface of the porous dispensing member that contacts the skin if the dispensing member is pressed against the skin.

A disadvantage of this known apparatus is that the structure for controlling the rate at which liquid is dispensed is relatively complicated. Furthermore, the liquid in the porous dispensing member is exposed to the environment over a relatively large surface and the viscosity of the liquid has a relatively important influence on the rate at which the liquid is dispensed. Furthermore, the return of liquid from the dispensing member increases the risk of contamination. The use of a disinfectant to reduce such risks increases the risk of causing skin irritation and/or allergic reactions.

From U.S. Pat. No. 4,031,618, a shaving device with an integral lotion dispensing means is known. The dispensing means comprises a lotion chamber having a flexible membrane wall. A rotating cam driven by the motor of the shaver repetitively pushes the membrane and thereby urges lotion out of the chamber and through the liquid channel. The dispensing means can are turned on and off with the motor of the shaver. Thus, it is not possible to shave without lotion being dispensed unless the chamber is empty. Also the rate at which lotion is dispensed cannot be controlled.

From German patent application 1 703 761, another electric shaver with a liquid dispenser for applying liquid to the skin while shaving is known. The liquid is applied either by rolling a roller of liquid absorbing material over the skin or by spraying the liquid through or from the shaving head of the shaver. It is not described whether or how the amounts of dispensed liquid are controlled.

It is an object of the invention to provide a more simple solution for controlling the rate at which liquid is dispensed from a motorized personal care device in which motion for dispensing the liquid is transferred from the motor for driving the device. A further object is to provide a solution which does not require the return of liquid to the container.

According to the invention, this object is achieved by providing an electric personal care device according to claim 1.

By controlling amounts of movement transmitted from the motor for driving the device to at least the movable part of the pump such that, in the first and second operating conditions, different amounts of movement are transmitted by the transmission to at least the movable part of the pump, the rate at which liquid is dispensed can be controlled in a simple manner.

Figure 2:
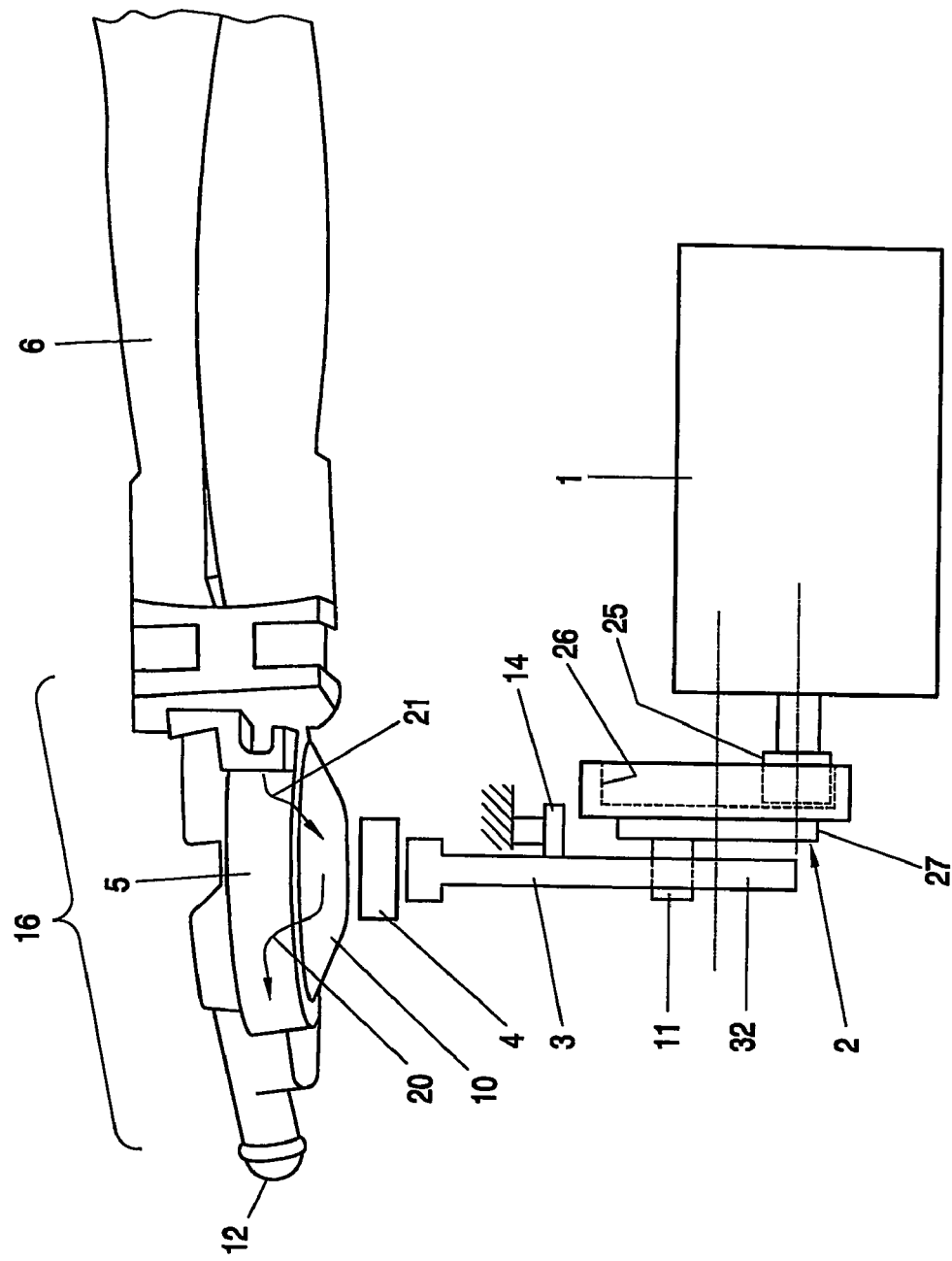
Figure 3:
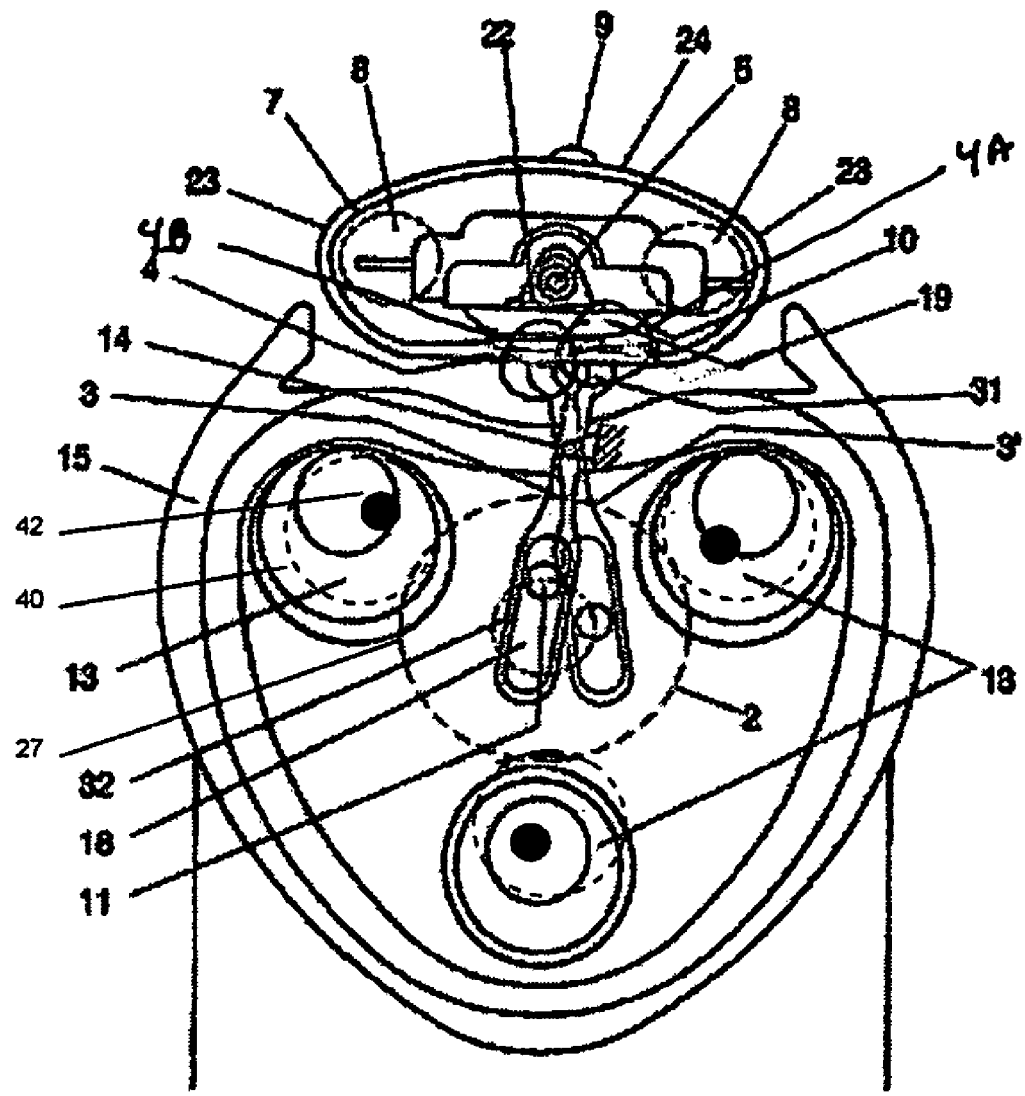

Specific embodiments of the invention are set forth in the dependent claims. Further aspects, effects and details of the invention are described with reference to the attached drawing, in which:

FIG. 1 schematically shows a partially cutaway side view of an example of an embodiment of a hair removing apparatus according to the invention, FIG. 2 schematically shows an exploded view of the pump of the example shown in FIG. 1 in more detail, and FIG. 3 schematically shows a partially cutaway front view of the pushing member of the example shown in FIG. 1.

The example of a personal care device according to the invention shown in the drawing is an electric shaver. The shaver has a housing 15 with three hair removing devices, in the present example shaving heads 13 for shaving off hair of a part of the skin, for example facial hair. In use, the shaving heads 13 are driven by an electromotor 1. These and various other types of shaving heads, which may include rotating or oscillating knives, and driving structures thereof are known as such in the art and therefore not described in detail.

The housing 15 accommodates a liquid reservoir 6 connected via a liquid channel 16 to a liquid outlet 12. The liquid channel 16 is provided with and extends through a pump 5 for pumping liquid, such as shaving lotion or cream, through the channel 16 to the liquid outlet 12. The pump 5 has a resilient wall 10 partially enclosing an internal space 19 that is part of the liquid channel 5. According to the present example, the pump 5 is a membrane pump, as is known per se in the art.

For transferring motion from the motor 1 to the pump 5 and to the shaving heads 13, the shaver includes a transmission coupled to the motor 1 and to movable parts of the pump 5 and of the shaving heads 13. Thus, the same transmission assembly is used for driving both the pump 5 and the hair removing assembly 13.

The transmission includes a toothed distribution gear wheel 2 coupled via internal teeth 26 to a pinion 25 on a drive shaft 17 of the motor 1. External teeth 27 of the distribution gear wheel 2 engage pinion wheels 40 on drive shafts 42 of the shaving heads 13. The transmission further includes a drive pin 11 positioned off-center on a face of the distribution gear wheel 2 facing away from the drive shaft 17, which drive pin 11 engages in a slot 18 in a proximal end 32 of an elongate pushing member 3. The pushing member 3 is pivotably suspended to the housing by a journal pin 14 spaced from the position where the drive pin 11 engages the pushing member 3. In operation, the motor 1 causes its drive shaft 17 to rotate. The drive shaft 1 drives rotation of the distribution gear wheel 2. In turn, the distribution gear wheel 2 entrains the pinions on the drive shafts of the shaving heads so that the knives of the shaving heads are rotated for cutting off hairs projecting through slots in the stationary screens of the shaving heads 13. Furthermore, rotation of the drive pin 11 about the axis of the distribution gear wheel 2 causes an oscillating movement of the pushing member 3 about the journal pin 14. This results in a pendular motion of the distal end 31 of the pushing member 3 opposite its proximal end 32 between a pushing position and a return position.

In the pushing position (shown in fall lines in FIG. 3), the pushing member 3 keeps the resilient wall 10 displaced inwardly with respect to the internal space 19 compared with a position of the resilient wall 10 when the pushing member is in its return position 3' (shown in dot-and-dash lines in FIG.

3). According the present example, this effect is achieved since the pushing member 3 in its pushing position pushes against the control member 4, which is thereby displaced towards the resilient wall 10. In turn, the control member 4 pushes against the resilient wall 10 causing that wall to be displaced inwardly with respect to the internal space 19. When the pushing member 3 moves to its return position 3', the control member 4 and the resilient wall 10 are allowed to return from the inwardly displaced position towards a more outwardly located position.

In operation, the oscillating movements of the pushing member 3 cause the volume of the internal space 19 to vary accordingly in an oscillating manner. In combination with the action of one way valves upstream and downstream from the internal space 19 allowing liquid flow in downstream direction only (or at least restricting it less than in upstream direction), the variations of the volume of the internal space 19 result in a pumping action as indicated by arrows 20, 21 in FIG. 2, causing liquid in the channel 5 to flow towards the outlet 12.

In the present example a membrane 22 forms the one-way valve. However, it is likewise possible to use other type of pumps driven by the motor via a transmission that also drives the hair removing means.

Electrically connected to the electromotor 1 is a switch 126 on the outside of the housing 15 with which the electromotor 1 can be switched "on" and "off".

The control member 4 is arranged to control the displacement of the resilient wall 10 between the positions associated with the pushing and return positions of the pushing member 3 such that, in different operating conditions, a movement of the pushing member 3 from the pushing position to the return position and back causes different amounts of displacement of the resilient wall 10.

As is shown in FIGS. 2 and 3, the control member of the control structure is positioned between the resilient part 10 and the pushing member 3. The pushing member 2, control member 4 and the resilient part 10 are positioned such that, in use, the pushing member 3 and the resilient wall 10 are in contact with the control member 4 during at least a part of the pumping cycle. Thus during at least a part of the pumping cycle, the pushing member 3 pushes the resilient wall 10 inwardly.

The control member 4 has a thickness in the pushing direction from the pushing member 3 to the resilient part 10 that varies in a direction transverse to the pushing direction. Moreover, control member is movable in the transverse direction with respect to the pushing member 3 and the resilient wall 10. Thus, the thickness of the portion of the control member 4 located between the pushing member 3 and the resilient wall 10 and contacting these parts, when the apparatus is in operation, can be varied. If a thin portion of the control member 4 is located between the pushing member 3 and the resilient wall 10 and contacts these parts as shown in 4A, when the apparatus is in operation, a part of the pushing motion of the distal end 31 of the pushing member 3 most remote from the resilient wall 10 is not transferred to the resilient wall 10. Accordingly some of the pushing motion is lost and only a portion of the pushing motion is transferred to the resilient wall 10. This results in a reduced pumping action of the pump 5. The thicker the portion of the control member 4 that is located between the pushing member 3 and the resilient wall 10 and that contacts these parts as shown in 4B, when the apparatus is in operation, the less pushing motion is lost and the more intensive the pumping action and, hence, the rate at which liquid is dispensed is. Conversely, it can be provided that, if the control member 4 is completely shifted out of the range of movement in which the pushing member 3 tumbles, there is no pumping action at all.

According to the present example, the control member 4 is wedge-shaped. This allows a continuously variable rate at which the liquid is dispensed. Moreover, the direction in which the thickness of the wedge-shaped control member 4 increases coincides with the direction in which the distal end 31 of the pushing member 2 moves transversally to the pushing direction as it moves from the return position to the pushing position. This causes the pumping action to be increased and even allows to use a pushing member that does not move in pushing direction when moving from the return position to the extended position. The extended position would then only be more extended than the return position in the sense that it causes the control member to move in pushing direction.

Since the control member 4 is movable in a direction transverse to the pushing direction from the pushing member 3 to the resilient wall 10 it is not prone to being displaced due to the pushing action by the pushing member 3.

As is shown in FIG. 3, a strip 7 projects from the control member 4 in a direction transverse to the pushing direction. Thus, a simple solution is provided for operating the control member 4 a position spaced from the control member 4, for instance, as in the present example, at the outside of the housing 15.

Furthermore, a portion of the strip 7 remote from the control member 4 extends along a curve 23 contiguous with a next operable portion 24 of the strip 7 extending along an operating path. Portions of the housing 15 directly adjacent to the operating path extend parallel to directly adjacent portions of that operating path. Thus, the position of the control member 7 can easily be controlled by shifting an operable portion 24 of the strip 7 along directly adjacent portions of the housing 15, similar to the way a thumb wheel is operated. To further facilitate operation, the operable portion 24 of the strip 7 is provided with a knob 9.

Since the curved portion 23 of the strip 7 extends about the pump and is contiguous with the operable portion 24 extending along the operating path, the control member 4, which is located in a position between the pump 5 and the transmission, can be operated from a position at the outside of the pump 5.

A particularly positive control over the control member 4 is obtained because the strip 7 is part of an endless-belt formed by the strip and the control member 4, the strip 7 having portions extending form the control member 4 in opposite directions. The control member may also be attached to an endless belt formed by the strip. The endless belt passes over two guiding cams 8. Thus, by circulating the endless-belt 7 around the guiding cams 8, the control member 4 can be displaced transverse to the pushing direction in a direction in which its thickness varies and to vary the flow rate of pumped liquid.

According to the present example, the liquid reservoir 6 and the liquid channel 16 can be removed and replaced with other devices. The pushing member is also connectable to other electrical devices. In particular, the shown pushing member 3 and driving thereof are especially suited for connection to hair trimmer for driving the hair trimmer. This allows either to replace the liquid dispensing assembly by a hair trimming assembly or at least provides a modular construction in which a large number of identical parts can be shared between different models of hair removing apparatus having either a hair trimmer or a liquid dispensing assembly.

It should be noted that while the invention is described by way of an example as implemented in a shaving device, the invention could likewise be applied in other hair removing apparatus such as hair trimming or epilating devices, or in oral care devices such as toothbrushes. Furthermore, it should be noted that the above-mentioned embodiments illustrate rather than limit the invention, and that those skilled in the art will be able to design many alternatives without departing from the scope of the appended claims. For instance, the pump may be arranged in a channel between the liquid reservoir and the environment, to generate a pressure in the liquid reservoir, which in turn causes liquid to be urged through the liquid channel to the liquid outlet. In the claims, any reference signs placed between parentheses shall not be construed as limiting the claim. The word 'comprising' does not exclude the presence of other elements or steps than those listed in a claim. The mere fact that certain measures are recited in mutually different claims does not indicate that a combination of these measures cannot be used to advantage.

The invention claimed is:

1. An electric personal care device for dispensing a liquid, comprising:
    a housing having a liquid outlet;
    a liquid channel leading to the liquid outlet;
    a pump for causing liquid displacement through the liquid channel to the liquid outlet;
    a motor operatively coupled to the device for driving movement of at least a movable part of the device; and
    a control structure having an inclined surface operable between at least a first position on the inclined surface and a second position on the inclined surface; and
    a rod, arranged between the motor and the control structure, wherein the control structure is arranged between the rod and a resilient wall of the pump communicating with or part of the liquid channel, wherein the rod is movable by the motor between a pushing position and a return position, in which pushing position the rod keeps the resilient wall displaced inwardly compared with a position of the resilient wall when the rod is in its return position, and wherein the inclined surface of the control structure is arranged to control the displacement of the resilient wall between the pushing and return positions of the rod such that, different amounts of displacement of the resilient wall occurs between the first and second positions on the inclined surface.

2. An electric personal care device for dispensing a liquid, comprising:
    a housing having a liquid outlet;
    a liquid channel leading to the liquid outlet;
    a pump for causing liquid displacement through the liquid channel to the liquid outlet;
    a motor operatively coupled to the device for driving movement of at least a movable part of the device;
    a transmission coupled to the motor to be driven thereby and coupled to the pump for imparting movement to at least a movable part of the pump while in an 'on' condition, thereby causing pumping action by the pump;
    and a control structure operable between at least a first and a second operating condition for dispensing liquid at different rates;
    wherein the control structure is arranged for controlling amounts of movement transmitted by the transmission to at least the movable part of the pump such that, in the first and second operating conditions, different amounts of movement are transmitted by the transmission to at least the movable part of the pump,
    wherein the pump has a resilient wall at least partially enclosing an internal space communicating with or part of the liquid channel; the transmission further comprises a pushing member which is at least partially movable between a pushing position and a return position, in which pushing position the pushing member keeps the resilient wall displaced inwardly with respect to the internal space compared with a position of the resilient wall when the pushing member is in its return position;
    wherein the control structure is arranged to control the displacement of the resilient wall between the positions associated with the pushing and return positions of the pushing member such that, in said first and second operating conditions, different amounts of displacement of the resilient wall between the positions associated with the pushing and return positions of the pushing member are caused; and
    wherein said control structure comprises a control member of which a portion is located between said pushing member and said resilient wall, said portion between said pushing member and said resilient wall having a different thickness in a direction from the pushing member to the resilient wall.

3. A device according to claim 2, wherein said control member is movable in a direction transverse to said direction from the pushing member to the resilient wall.

4. A device according to claim 2, wherein said control member is wedge-shaped.

5. A device according to claim 2, wherein said control structure further comprises a strip projecting from said control member in a direction transverse to said direction from the pushing member to the resilient wall.

6. A device according to claim 5, wherein a portion of said strip remote from said control member extends along a curve contiguous with a next operable portion extending along an operating path, and wherein the device has a housing of which portions directly adjacent to said operating path extend parallel to directly adjacent portions of said operating path.

7. A device according to claim 6, wherein at least a portion of the liquid channel is disconnectable from and reconnectable to the device.

8. A device according to claim 5, wherein a portion of said strip remote from said control member extends along a curve about said pump and contiguous with a next operable portion extending along an operating path.

9. A device according to claim 5, wherein the strip is part of or forms an endless-belt having portions extending from the control member in opposite directions.

10. A device according to claim 2, wherein a distal portion of the pushing member in at least one of said pushing and return positions pushes towards said resilient wall.

* * * * *